(12) United States Patent
Bozdog et al.

(10) Patent No.: US 10,030,971 B2
(45) Date of Patent: Jul. 24, 2018

(54) MEASUREMENT SYSTEM AND METHOD FOR MEASURING IN THIN FILMS

(71) Applicants: GLOBALFOUNDRIES, Inc., Grand Cayman (KY); Nova Measuring Instruments Ltd., Rehovot OT (IL)

(72) Inventors: Cornel Bozdog, San Jose, CA (US); Alok Vaid, Ballston Lake, NY (US); Sridhar Mahendrakar, Clifton Park, NY (US); Mainul Hossain, Clifton Park, NY (US); Taher Kagalwala, Clifton Park, NY (US)

(73) Assignees: Globalfoundries, Inc., Grand Caymen (KY); Nova Measuring Instruments Ltd., Rehovot (IL)

( * ) Notice: Subject to any disclaimer, the term of this patent is extended or adjusted under 35 U.S.C. 154(b) by 0 days.

(21) Appl. No.: 15/228,772

(22) Filed: Aug. 4, 2016

(65) Prior Publication Data

US 2017/0038201 A1 Feb. 9, 2017

Related U.S. Application Data (60) Provisional application No. 62/200,698, filed on Aug. 4, 2015.

(51) Int. Cl.
*G01B 15/02* (2006.01)
*G01N 23/22* (2018.01)
(Continued)

(52) U.S. Cl.
CPC .......... *G01B 15/02* (2013.01); *G01B 11/0625* (2013.01); *G01N 23/2273* (2013.01);
(Continued)

(58) Field of Classification Search
CPC ............... G01B 15/02; G01N 2223/61; G01N 2223/6116; G01N 23/2273
See application file for complete search history.

(56) References Cited

U.S. PATENT DOCUMENTS 6,650,424 B2 11/2003 Brill et al.
9,330,985 B2 * 5/2016 Vaid .................. H01L 22/12
(Continued)

OTHER PUBLICATIONS

Cunff D., et al., "In-line metrology capability for epitaxial multi-stack SiGe laers," 2012 SEMI Advanced Semiconductor Manufacturing Conference, IEEE, 2012, pp. 115-121.
(Continued)

*Primary Examiner* — Mark R Gaworecki (57) ABSTRACT

A measurement method and system are presented for in-line measurements of one or more parameters of thin films in structures progressing on a production line. First measured data and second measured data are provided from multiple measurements sites on the thin film being measured, wherein the first measured data corresponds to first type measurements from a first selected set of a relatively small number of the measurement sites, and the second measured data corresponds to second type optical measurements from a second set of significantly higher number of the measurements sites. The first measured data is processed for determining at least one value of at least one parameter of the thin film in each of the measurement sites of said first set. Such at least one parameter value is utilized for interpreting the second measured data, thereby obtaining data indicative of distribution of values of said at least one parameter within said second set of measurement sites.

13 Claims, 9 Drawing Sheets

(51) Int. Cl.
*G01B 11/06* (2006.01)
*G01N 23/2273* (2018.01)
*H01L 21/66* (2006.01)
*H01L 27/12* (2006.01)

(52) U.S. Cl.
CPC .......... *H01L 22/20* (2013.01); *G01B 2210/56* (2013.01); *G01N 2223/61* (2013.01); *G01N 2223/6116* (2013.01); *H01L 27/12* (2013.01)

(56) References Cited

U.S. PATENT DOCUMENTS

| | | | |
|---|---|---|---|
| 2013/0203188 A1* | 8/2013 | Vaid | G01B 21/00 438/14 |
| 2013/0245806 A1* | 9/2013 | Vaid | H01L 22/20 700/108 |
| 2014/0273299 A1* | 9/2014 | Vaid | H01L 22/26 438/14 |
| 2015/0032398 A1 | 1/2015 | Peterlinz et al. | |
| 2015/0198435 A1 | 7/2015 | Vaid et al. | |
| 2016/0141193 A1 | 5/2016 | Pandev et al. | |
| 2016/0293407 A1* | 10/2016 | Dubois | H01L 21/0206 |

OTHER PUBLICATIONS

Vaid A., et al., "Hybrid enabled thin film metrology using XPS and optical," SPIE Advanced Lithography, International Soceity for Optics and Photonics, 2016, vol. 9778, pp. 97780M-97780M-11.
ISR/Israel Patent Office, "International Search Report and Written Opinion of the International Search Authority," Application No. PCT/IL2016/050851, dated Nov. 7, 2016, 10 pages.

* cited by examiner

MEASUREMENT SYSTEM AND METHOD FOR MEASURING IN THIN FILMS

CROSS REFERENCE TO RELATED APPLICATION(S)

This application claims priority under 35 USC 119(e) to U.S. Provisional Application Ser. No. 62/200,698, filed on Aug. 4, 2015, the content of which is incorporated herein by reference.

TECHNICAL FIELD

The present invention is in the field of measurement techniques, and relates to a measurement system and method, particularly useful for controlling a process of manufacture of structures/samples containing thin films, such as semiconductor wafers.

BACKGROUND

Advanced semiconductor industry is continuing to integrate thinner and multi-stack films of novel material compositions (e.g. SiGe, HKMG, 3D FinFet, etc.). This is one way to continue the performance scaling to ensure that advanced nodes like 1X and beyond keep following the Moore's law.

Process control of ultra-thin films in the 1-2 nm range require a Total Measurement Uncertainty (TMU1—relative accuracy metric) and Fleet Matching on the order of 0.1 A. Optical metrology techniques (such as Spectral Ellipsometry—currently the throughput-intensive workhorse of thin film measurements) are reaching their performance limits. As an example, ability to accurately identify 0.1 Angstrom change in film thickness is fundamentally limited by crosstalk with other parameters of the film stack (thickness of other layers, variable materials composition) as well as limited optical sensitivity.

There is a need in the art in a novel approach for monitoring/measurement thin films' parameters, especially for the films having changeable parameter(s) such as for example material concentration. Moreover, the monitoring technique should preferably enable effective process control of the manufacture of thin film based structures progressing on a production line. In other words, the measurement technique should be effectively operable in real-time (or in-line or on-tool) measurement mode. In this connection, it should be noted that the term "in-line" or "on-tool" used herein refers to a measurement mode which is an alternative to a measurement by a stand-alone measurement tool operating in an off-line mode.

Figure 1:
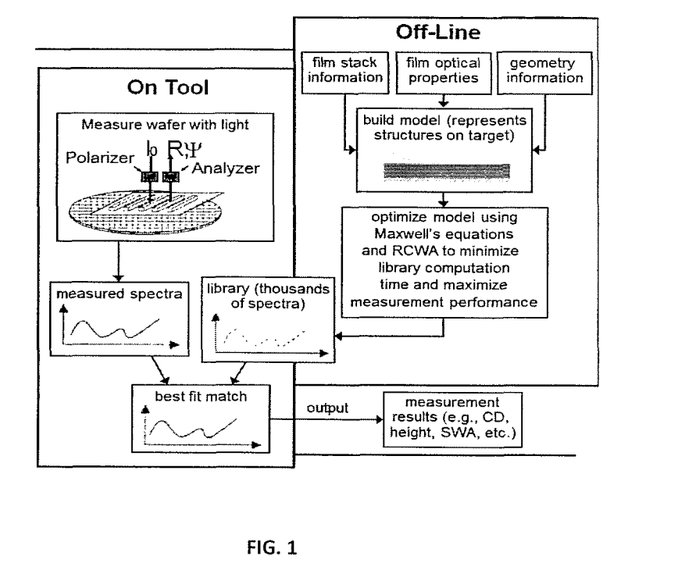
FIG. 1 is a schematic illustration of the general principles of the known scheme for optical measurements, such as e.g. using OCD tool based on Spectral Reflectometry.

Optical metrology techniques are based on measurement of properties of light reflected from a sample. For thin film measurements, they rely on the contrast between optical properties of different films to model, de-convolute and individually extract the film thickness, and are typically extended to profile measurements of periodic structures using the properties of scattered light (scatterometry, also known as optical critical dimension—OCD). While such methods are fast and well suited for advanced process control (APC), they rely on assumptions about optical properties and geometry. In particular, the performance for ultra-thin films with variable composition is typically subjected to errors due to inability to separate the effects of optical properties changes from thickness change. This is schematically illustrated in FIG. 1 showing the diagram of an optical measurement and data interpretation of a planar or periodic structure.

The figure shows, in a self-explanatory manner, the on-tool (or on-line) and off-line measurement schemes. In the on-line measurement scheme, optical spectral measurements (e.g. polarized based measurements) are applied to a sample (e.g. semiconductor wafer), and a fitting procedure is applied to measured spectral data and upon identifying the best-fit spectral data from the library, determining the corresponding structure parameters (e.g. CD, height, SWA, etc.). As also shown in the figure, the spectral library is built using off-line measurement scheme. The off-line measurement scheme utilizes the model creation (modeled structures on target) using such input data as film stack information, film optical properties, and geometry information. The model may then be optimized using various known approaches, for creating/updating the spectral library, i.e. theoretical spectral data.

Figure 2:
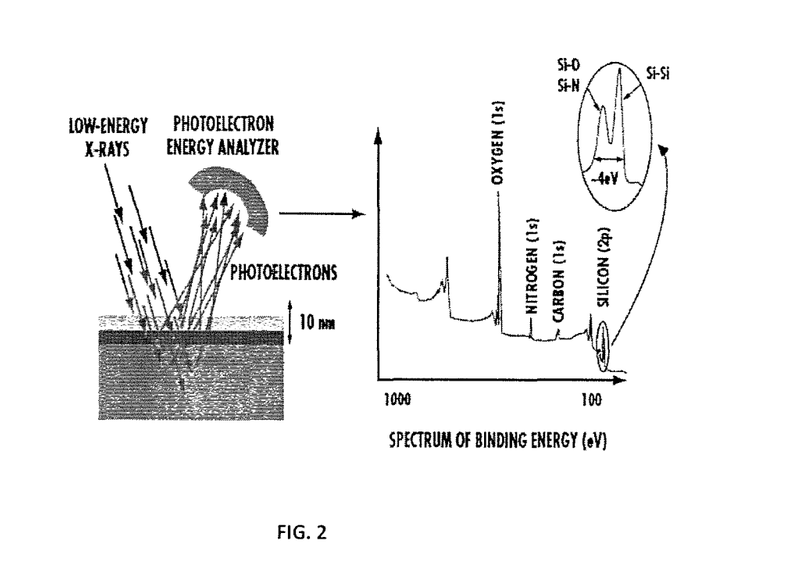
FIG. 2 is a schematic illustration of the general principles of the known scheme for XPS measurements.

X-ray methods come in different flavors. Particularly suitable for thin films, X-Ray Photoelectron Spectroscopy (XPS) measures the spectral response of photoelectrons generated by X-Ray irradiation of the target. Such photoelectrons are rapidly recombining inside the material, the net effect being that only electrons generated in the superficial ~10 nm of material are able to escape the stack and be detected. Signals from different atomic species/molecules are recorded as a function of energy and ascribed to different layers of the stack, consistent with the physical interaction between X-Rays, electrons and the different materials. This is illustrated schematically in FIG. 2 showing, in a self-explanatory manner, a diagram of an XPS measurement and measured data. XPS measurements can thus independently extract both composition (relative number of atoms of different species) and layer thicknesses of multi-layer ultra-thin films. However, XPS technique does not provide desirable throughput required for high volume manufacturing (HVM). In other words, the XPS measurements are practically unsuitable for on-line measurements mode on structures progressing on a production line for the production process control.

Figure 3A:
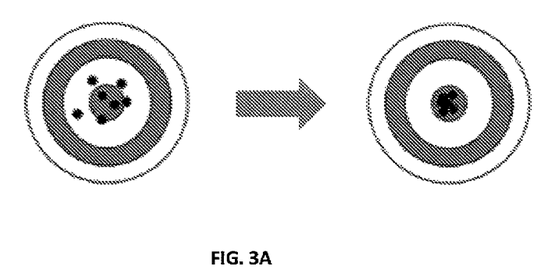
FIGS. 3A and 3B demonstrate the effect of measurement uncertainty on the HVM.
Figure 3B:
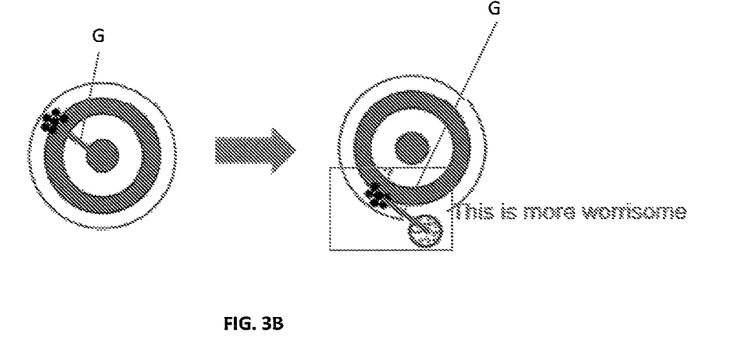

Reference is made to FIGS. 3A and 3B demonstrating the effect of measurement uncertainty on the HVM. FIG. 3A shows measurement subjected to precision (type A) errors, which can be typically minimized by reducing the number of floating parameters. FIG. 3B shows measurement subjected to accuracy (type B) errors. Any measurement is subject to different sources of errors. According to the specific circumstances of model-based metrology, type A errors are easily quantifiable based on statistical analysis of random noise—precision. This type of error is typically minimized by reducing the number of possible varying model parameters (and correspondingly increasing the stability of values for the key parameters when performing repeat measurements). Type B errors (accuracy indicator) typically arise from crosstalk between key parameters (floating) and some of the fixed parameters (whole corresponding physical sample parameters actually change). Such fixed parameters can include optical properties of materials. In HVM environment, such errors are largely hidden, and can lead to incorrect wafer disposition. As shown in FIG. 3B, comparison to reference can help establish the correlation calibration to "truth" (arrow G) during recipe setup. However, inadvertent (unknown) changes in some of the fixed model parameters during HVM can induce corresponding changes in the measured values; this invalidates the original relationship to the "truth" and thus can trigger incorrect wafer disposition.

Let us define a "reference-level" measurement as being invariant to inadvertent changes in other parameters as resulting from normal process changes in HVM and at the same time being super sensitive to measurement parameters in question. Examples of such measurement can be considered X-Ray Fluorescence (XRF) which provides the total number of atoms of a certain species regardless of atoms from other species present in the measured sample, or XPS which probes the atomic species present in the superficial layers of the sample regardless of the layer stack beyond ~10 nm in depth. Ideally, in-line metrology would provide a "reference-level" measurement. In practice, there is always a trade-off between measurement speed and performance, which in many cases is solved in favor of the higher throughput, higher risk metrology.

Hybrid Metrology is the practice of combining two or more metrology tools that measure the same or similar structures. Data is shared between toolsets in complementary way to enhance metrology performance, and enables measurement of complex structures that cannot be measured with enough performance by any of the individual toolset. Most of hybrid metrology work to date combined non-reference metrologies (CD-SEM and OCD).

SUMMARY

The present invention provides a novel Hybrid Metrology solution for thin film measurements, based on the combination of X-Ray based technologies and optical methods. This is a combination of slow and accurate reference-level metrology (XPS) with rapid and precise non-reference (optical), combination of XPS and optical to allow measurement of thin films and composition on structures.

The technique of the invention provides a so-called hybrid-enabled smart sampling (HESS) measurement technique. This is associated with the following: Tighter process windows require better control of process variability across the sample (e.g. wafer) as well as "hot spot" detection and edge monitoring. Higher measurement sampling rates are desired, with higher, quality level performance. To mitigate the trade-off between speed and performance, the invention explores hybrid combinations of XPS and optical methods, where XPS uses a "sparse sampling plan" and optical uses a "dense, full-wafer sampling". The technique of the invention extends the XPS performance to full wafer map with improved throughput provided by the optical method.

More specifically, the invention extends measurements with limited sample set to larger sampling (optical measurements). This technique is generally applicable for case of several (relatively low number) high accuracy (trusted, slow) measurements and a lot (relatively high number) of fast optical measurements. Such relatively slow high-accuracy measurements may include one or more of the following techniques: XPS, X-ray Fluorescence (XRF), Transmission Electron Microscopy (TEM), Focused Ion Beam (FIM), Secondary Ion Mass Spectrometry (SIMS). The relatively fast measurements are optical measurements which may be based for example on Spectral Reflectometry, Polarized Spectral Reflectometry, etc.

It should be understood that for the purposes of this disclosure, the "relatively slow" and "relatively fast" measurements and corresponding measurement systems are distinguished from one another in that the "slow" measurements need more time to collect and interpret measured data but provide higher accuracy, as compared to those of the "fast" measurements. Accordingly, in the invention, the "relatively slow" and "relatively fast" measurements are applied to, respectively, a much smaller number N of measurement locations/points/sites and much higher number M of measurement locations/points/sites, such that M=N+K (K being integer starting from 1).

Preferably, the measurement locations are selected such that N locations of the slow measurements (generally at least two such locations) $L_1 \ldots L_n$ are included in the M locations of the fast measurements, i.e. $L_1, \ldots L_n, L'_1, L'_2, L'_k$.

The measurement sites/locations of at least the fast measurements are preferably selected to be substantially uniformly distributed within the structure under measurements. For example, considering a typical semiconductor wafer (i.e. disk-like structure), the "fast" measurement locations are substantially uniformly distributed along the radius of the wafer (i.e. to include the locations of the central and periphery regions).

The fast measurements are trained against the high accuracy slow measurements. Training per structure (wafer) enables to eliminate several main reasons for optical tool inaccuracies such that external and internal calibration issues, as well as wafer loading tilts are not relevant anymore. Practically, a measurement optical system can be simple, where only raw spectrum collection and training are needed, while such requirements as special alignments, NA issues, are eliminated, as well as tool-to-tool matching for the optical system is not required. The use of multiple measurements channels and polarization-based measurements might be beneficial, but they do not need a match from system to system.

Thus, the technique of the invention eliminates most inaccuracies of calibration, tool matching, alignment, etc. (which normally require highly specialized Best Know Methods). In addition, it enables to eliminate modeling. Also, it eliminates a risk that the training design of experiment (DOE) is not sufficient to include the sample measured (because there is no DOE—the sample itself is the DOE). The technique provides extension for any reference metrology (slow) to much larger coverage using measured spectra acting as "virtual reference" after per-wafer training.

Thus, according to one broad aspect of the invention, there is provided a measurement method for in-line measurements of one or more parameters of thin films in structures progressing on a production line. The method comprises:

providing first measured data and second measured data from multiple measurements sites on the thin film being measured, wherein the first measured data corresponds to first type measurements from a first selected set of a relatively small number of the measurement sites, and the second measured data corresponds to second type optical measurements from a second set of significantly higher number of the measurements sites;

processing the first measured data and determining at least one value of at least one parameter of the thin film in each of the measurement sites of said first set;

utilizing said at least one parameter value for interpreting the second measured data, thereby obtaining data indicative of distribution of values of said at least one parameter within said second set of measurement sites.

Preferably, the measurement sites of the second set are selected to be substantially uniformly distributed within the thin film being measured.

Preferably, the second set of the measurement sites includes the first set of the measurement sites.

In some embodiments of the invention, the above procedure of utilizing the at least one parameter value for interpreting the second measured data includes: identifying a matching set between the measurement sites in the first and second measured data; creating a temporary trained recipe for the matching set; and using the temporary trained recipe to interpret the second measured data.

In some embodiments, the first set of the measurement sites is selected to enable measurement of minimal and maximal values of the at least one parameter of interest. In some examples, the selection is based on prior knowledge about a shape of variation of the at least one parameter of the thin film across the structure.

In some embodiments, the method of the invention is used for measurements in semiconductor wafer structures.

As indicated above, the first type measurements and second type measurements are different in at least time required for collection and interpretation of measured data, where the first type measurements are relatively slow measurements and the second type measurements are relatively fast measurements. Preferably, the first-type (slow) measurements are characterized by higher accuracy as compared to the second type measurements.

In some embodiments, the first type measurements comprise XPS. The second type measurements are optical measurements and may comprise Spectral Reflectometry.

According to another broad aspect of the invention, it provides a measurement method for in-line measurements of one or more parameters of thin films in structures progressing on a production line, the method comprising:

applying XPS measurements to a first selected set of a relatively small number of measurement sites in the thin film and providing XPS measured data;

applying optical measurements to a second set of significantly higher number of the measurements sites including the measurement sites of the first set and providing optical measured data;

processing the XPS measured data and determining a value for at least one parameter of the thin film in each of the measurement sites of said first set;

utilizing said at least one parameter value for interpreting the optical measured data, thereby obtaining data indicative of distribution of values of said at least one parameter within thin film, said distribution being indicative of quality of a process applied to said structure in production.

According to yet another broad aspect of the invention, it provides a system for use in the in-line measurements of one or more parameters of thin films in structures progressing on a production line. The system comprises:

a first measurement device configured and operable to perform first type measurements according to a first, sparse sampling plan, and provide first measured indicative of at least one parameter of the thin film in a first selected set of a relatively small number of measurement sites in the thin film;

a second optical measurement device configured and operable to perform second type measurements according to a second, dense sampling plan, and provide second measured indicative of at least one parameter of the thin film in a second set of significantly higher number of the measurements sites; and a control system configured to process the first and second measured data, the processing comprising processing the first measured data and determining at least one value of at least one parameter of the thin film in each of the measurement sites of said first set, and utilizing said at least one parameter value for interpreting the second measured data, thereby obtaining data indicative of distribution of values of said at least one parameter within said second set of measurement sites.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 4A to 4C schematically illustrate the principles of the present invention, where

FIGS. 5A to 5F exemplify measurements on a single layer film for the SiON case, where

FIGS. 6A and 6B exemplify measurements in a multilayer film stack, where

DETAILED DESCRIPTION

FIGS. 1 and 2 schematically demonstrate the general principles of the known schemes for, respectively, "fast" (in-line) optical measurements and measured data interpretation, and "slow" (off-line) X-ray measurements and measured data interpretation. FIGS. 3A and 3B demonstrate the effect of measurement uncertainty on the HVM.

As indicated above, the present invention provides a thin film measurement technique, suitable for on-line measurements, particularly useful for process control of the manufacture of thin film containing structures.

Figure 4A:
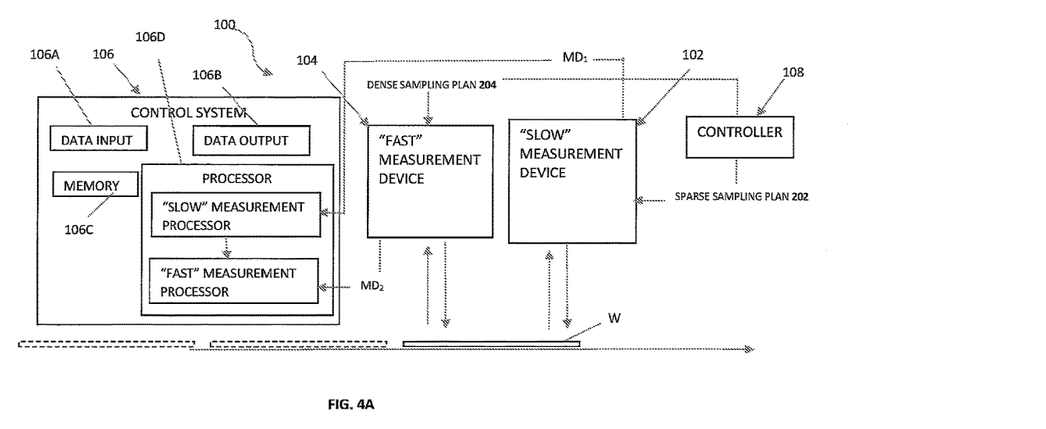
FIG. 4A shows a block diagram of a hybrid measurement system of the invention.
Figure 4B:
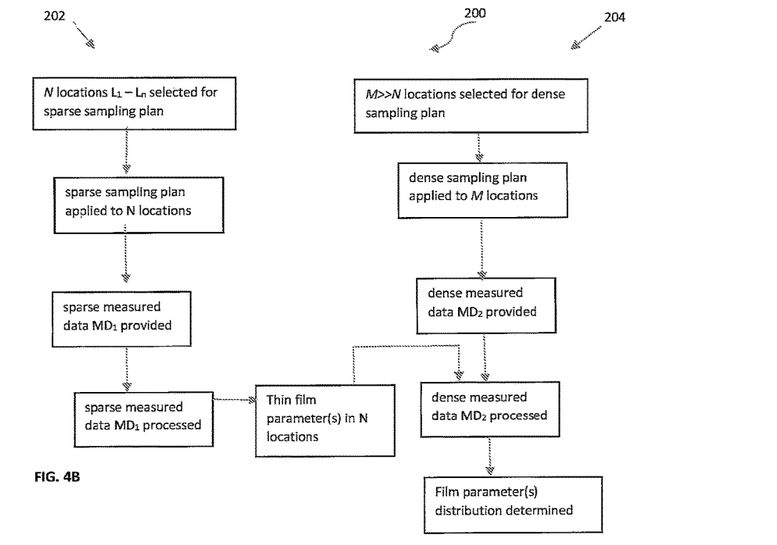
FIG. 4B shows a flow diagram of a measurement scheme utilized in such system.
Figure 4C:
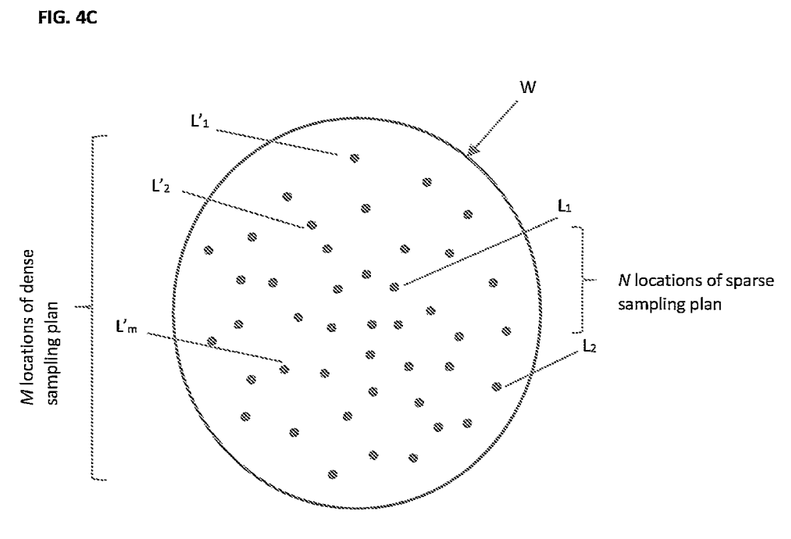
FIG. 4C exemplifies the arrangement of measurement sites/locations used for sparse and dense sampling plans.

Reference is made to FIGS. 4A to 4C schematically illustrating the principles of the present invention. FIG. 4A shows a block diagram of a hybrid measurement system 100 of the invention; FIG. 4B shows a flow diagram 200 of a measurement scheme utilized in such system; and FIG. 4C exemplifies the arrangement of measurement sites/locations used for sparse and dense sampling plans.

The measurement system 100 is configured to perform in-line measurements on thin-film containing structure progressing on a production line and may be aimed at process control of the production process being successively applied to the structures by a certain processing tool arrangement. More specifically, the present invention is used for process control used in the semiconductor industry and is therefore exemplified below with respect to this specific application.

It should, however, be understood that the principles of the invention are not limited to this specific application. Also, the invention is particularly useful for measurement of thin film parameters, e.g. unpatterned layers, and is therefore exemplified below as being used in measuring on the uppermost thin film layer on a wafer. Further, the invention is exemplified below as using XPS and optical measurements, as respectively, slow and fast measurements. However, as mentioned above, these are non-limiting examples of the respectively relatively slow and relatively fast measurement techniques distinguishing from one another by the factors defined above.

Thus, measurement system 100 is configured as a so-called automatic measurement system in the meaning that it is associated with a production-line processing tool arrangement (e.g. is integral with such tool arrangement) to be applied to a stream of wafers progressing on the production line. The measurement system includes such main constructional parts as a first measurement device 102 configured to apply first type of measurements, being relatively slow measurements, such as XPS measurements to a measurement site on the wafer, and a second optical measurement device 104 configured to apply second type of measurements, being relatively fast measurements, such as optical measurements to said measurement site. Also provided in the system is a control system 106 which receives and processes first and second measured data $MD_1$ and $MD_2$ corresponding to the slow and fast measurements and generates output data indicative of the structure parameter(s), e.g. relevant for the process control.

The control system 106 may be a separate computer system connectable (via wires or wireless signal transmission) to the output of the measurement devices 102 and 104 for receiving therefrom data indicative of/corresponding to the respective measured data; or may be part of either one of the measurement devices 102 and 103; or the data processing utilities of the computer system 106 may be distributed between these measurement devices. The control system 106 thus typically includes data input and output utilities 106A, 106B; memory utility 106C; and data processor and analyzer 106D; and may also include suitable communication/data formatting utilities.

Also provide in the system 100 is a controller 108 associated with the measurement devices 102 and 104 for operating these measurement devices to implement predetermined first and second measurement plans with respect to selected locations/sites on the structure. The controller 108 may or may not be part of the control system 106. The measurement scheme 200 implemented by the system 100 utilizes the combination of the first and second measurement plans which are, respectively, so-called "small sampling plan" (or "sparse sampling plan") 202 and "large sampling plan" (or "dense sampling plan") 204.

The sparse sampling plan 202 is applied by the relatively slow, high-accuracy measurements, which in the present example are constituted by XPS measurements performed by the measurement device 102. Thus, N locations (generally a few locations, e.g. N=2, locations $L_1$ and $L_2$) on the thin film layer of the wafer W are selected, and the XPS measurements are applied to these N locations. The N locations for the XPS measurements are preferably arranged with a relatively low spatial frequency (i.e. relatively large distance between them). The XPS measured data $MD_1$ is provided and processed to determine one or more parameters of the thin film in each of said N locations, e.g. thickness and/or certain material concentration. The so-determined parameter(s) of the thin film is/are used for "learning"/"training" mode with respect to the dense sampling plan measured data $MD_2$ (optical data).

The dense sampling plan 204 is based on optical measurements applied to a relatively larger number M (M>>N) of measurement locations/sites on the wafer MS arranged with a relatively high spatial frequency. Preferably, the M locations of the dense sampling plan 204 include the N locations of the sparse sampling plan 202 and additional K locations, i.e. M=N+K. The dense sampling plan measured data $MD_2$ is provided and the one or more desired parameters of the thin film determined is each of said N locations is/are used for interpreting (by fitting procedure) the optical measured data $MD_2$ to thereby determine the distribution of one or more thin film parameters within the structure.

It should be noted that the "training" mode or sparse sampling plan may be applied to a few similar structure for "learning" the optical data interpretation. For example, the training of optical measurements using e.g. XPS measurement(s) may be applied to 5 wafers (using 9 point map in each wafer), and this measured data $MD_1$ is used for determining the thickness and Nitrogen dose (Ndose) parameters in the uppermost layer (thin film) of the wafer. Then, the optical measurements of full wafer (e.g. 49 point map) is interpreted.

The following are some specific but not limiting examples of the measurement technique of the invention.

Figure 5A:
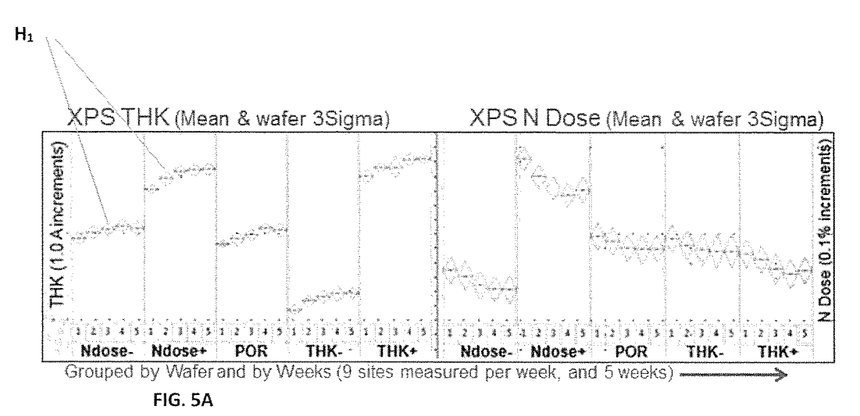
FIG. 5A shows design of experiment (DOE) set of 5 wafers measured by XPS over time.
Figure 5B:
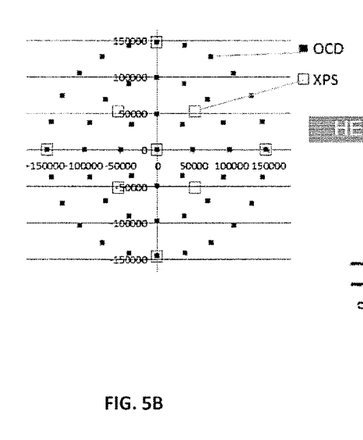
FIG. 5B shows the XPS and optical maps of measurement sites.
Figure 5C:
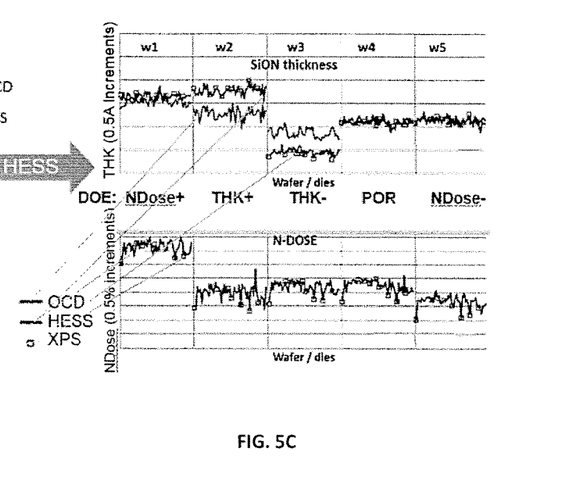
FIG. 5C shows HESS—SiON layer thickness measured by OCD tool, HESS and XPS, and N_Dose composition measured by HESS and XPS.
Figure 5D:
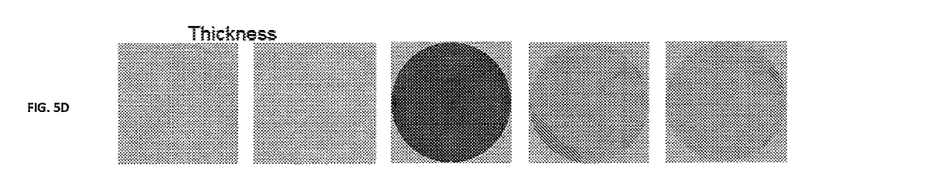
FIGS. 5D-5E show HESS Topography maps for 5 DOE wafers, for respectively SiON layer thickness and N-Dose composition.
Figure 5E:
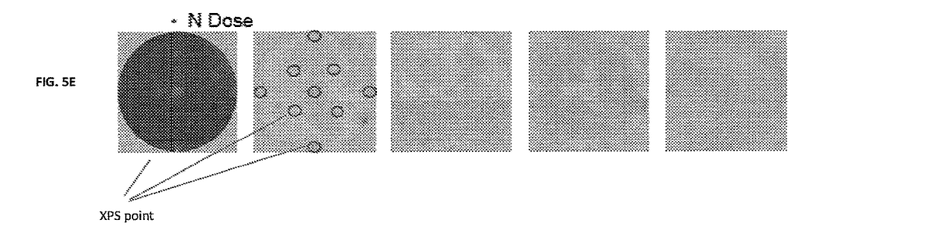
Figure 5F:
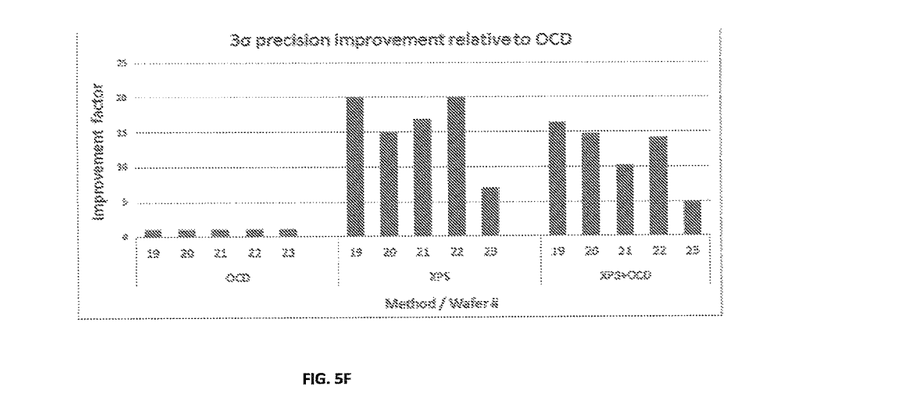
FIG. 5F shows the precision of XPS, thickness measured by OCD tool and HESS measurements.

FIGS. 5A to 5F exemplify measurements on a single layer film—the SiON case. FIG. 5A shows design of experiment (DOE) set of 5 wafers measured by XPS over a period of several weeks; FIG. 5B shows 5-point XPS map (N=5) and 49-point optical map (M=49); FIG. 5C shows HESS—SiON layer thickness (designated as OCD, HESS and XPS) and N_Dose composition (HESS and XPS); FIGS. 5D-5E show HESS Topography maps for 5 DOE wafers, for respectively SiON layer thickness and N-Dose composition; FIG. 5F shows that XPS/XPS_OCD (HESS) precision is 10× better than non-hybrid optical measurements precision for SiON stack.

In this example, a 5-wafer DOE (design of experiment) of SiON films deposited on silicon substrate is considered. The thicknesses and N-dose are varied between wafers based on process splits. XPS is the reference toolset for SiON. In a sequence of repeat measurements over several weeks (FIG. 5A, where plot $H_1$ represents the variability fingerprint across the wafers), the film and composition were measured, and also the slow outgassing of Nitrogen and the film growth are detected due to continued slow oxidation at the interface of dielectric/substrate.

The 9-point map data $MD_1$ measured using the XPS device 102 was combined with a 49-point full wafer map data $MD_2$ measured with the optical measurement device. Such map is illustrated in FIG. 5B. The results illustrated in FIG. 5C show that similar measurements using an optical technique alone (designated as OCD plot) demonstrate lower ability to identify the DOE conditions for thickness, even when the optical properties (related to N-dose) are fixed in the model due to low sensitivity. As indicated above, the term hybrid-enabled smart sampling (HESS) used herein refers to the methodology to combine/hybridize low (sparse) sampling measurements (example from reference tool) with high (dense) sampling measurements (example from workhorse tool) to allow cost effective but high performance metrology solution. The HESS methodology (HESS plot) shows substantially the same accurate measurement as the XPS method alone, for both thickness and N-dose composition.

The correspondence between the HESS and XPS graphs is further substantiated by topography maps for 5 DOE wafers shown in FIGS. 5D and 5E. The figure shows the circles representing the XPS points measured which are then extended by HESS to the whole wafer.

In addition to the striking accuracy improvement provided by HESS vs. standard optical method, the inventors have evaluated the precision improvement to a factor of ~10x, with HESS having similar precision to XPS (about 0.9% variability in thickness, and about 0.2% variability in N-dose). These results are showed in FIG. 5F: XPS/XPS_OCD (HESS) precision is 10 times better than non-hybrid optical measurements precision for SiON stack.

Figure 6A:
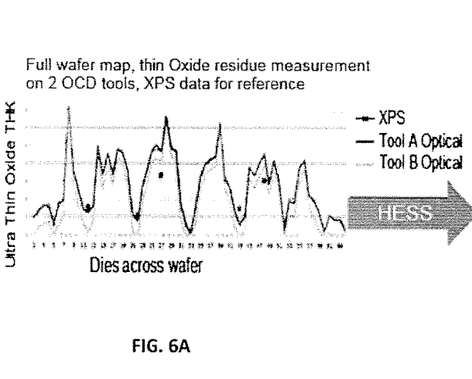
FIG. 6A illustrates the results using standard optical measurements with two toolsets.
Figure 6B:
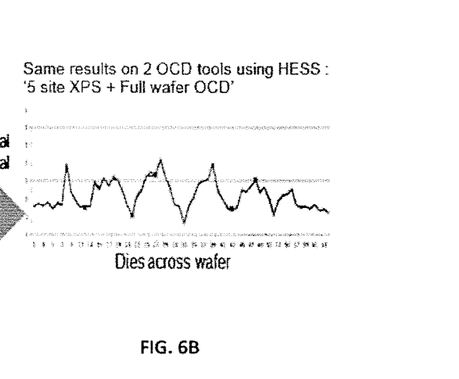
FIG. 6B illustrates HESS measurements with two toolsets.

FIGS. 6A-6B exemplify measurements in a multi-layer film stack. In this example, the case of an ultra-thin oxide residue on top of a SiN and SiO2 layer stack is considered. FIG. 6A illustrates the results using standard optical measurements with two toolsets showing differences between the two tools as well as difference with respect to the reference-level XPS measurement. FIG. 6B illustrates HESS measurements with two toolsets showing good matching to XPS, correct wafer map and tool matching improved as well. It is thus shown that by applying the principles of HESS to the sparse XPS data and dense optical data, the full wafer maps are not only improved, but also the matching between the two HESS tool results and the matching to reference is improved. When reference quality data is utilized in hybrid metrology, it is possible to observe measurement performance improvement on multiple attributes, such as accuracy and matching in this example.

Figure 7A:
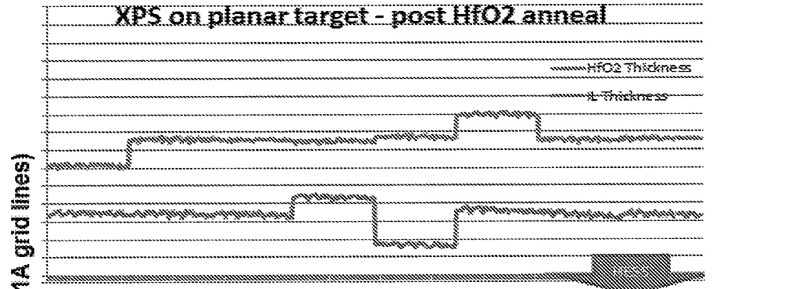
FIGS. 7A and 7B exemplify measurements on a planar stack including ultra-thin high k (HK) on top of ultra-thin interlayer (IL) dielectric layer.
Figure 7B:
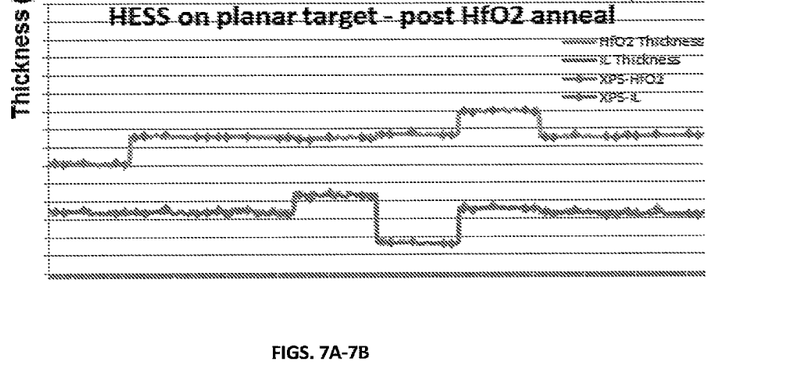

Reference is made to FIGS. 7A and 7B exemplifying the measurements on a planar stack including ultra-thin high k (HK) on top of ultra-thin interlayer (IL) dielectric layer. This example presents the most challenging layers within the RMG stack. Optical toolsets are typically challenged to correctly separate between the ultra-thin high-k and interlayer dielectric films (small thickness, relatively similar optical properties. This type of measurement falls well within the capability of XPS, where the photoelectron signals from SiO and HfO are not correlated. In an 8-wafer DOE, XPS identifies the DOE intent and correctly quantifies the thickness of the two layers (FIG. 7A). Using only 5 points per wafer for XPS, the HESS approach is applied using full wafer optical measurements and retrieves the similar measurement performance while reducing the measurement throughput overhead (FIG. 7B). As shown in the figures, 8-wafer DOE, XPS identifies the DOE intent and correctly quantifies the thickness of HfO$_2$ and IL (FIG. 7A); HESS on planar target sampling (5 sites of XPS and FWM of OCD) produce similar measurement performance as that of XPS: XPS (sparse sampling sites) track HESS thickness of HfO$_2$ and IL (FIG. 7B).

The inventors have demonstrated multiple applications (SiON, residue oxide and HK/IL) where the HESS methodology of the invention is utilized to combine sparse/limited XPS sampling with high optical across-wafer sampling to provide a cost effective and high performance metrology solution.

Thus, the present invention provides the novel approach, termed HESS approach, relating to "combined" or hybrid methodology where relatively slow/accurate measurement tool/device and relatively fast less accurate tool/device are used. XPS measurement device is an example of such slow/accurate tool. The XPS technique while being by itself capable of measuring the full wafer map with sufficient performance, required too much time to execute this. Therefore, considering in-line measurements applied to structures progressing on a production line, the invention uses the XPS as little as possible. A small sample set includes a few, in some examples minimum 5 points, to capture the minimal and maximal values of parameter of interest resulting from the manufacturing process. For example, if one knows that the across-wafer variation of a certain parameter of interest is typically U-shaped, then the center will be lowest point, and edges will be highest points, so the XPS measurements are applied to these points. In the case of M-shape, the center and mid-radius points are selected as the small sample set. Whatever XPS measured, this is the small sample set.

The second fast measurement tool is optical, e.g. Spectral Reflectometer. The corresponding spectra (center and edges, or center and mid-radius) are identified in the Spectral Reflectometry map (optical measured data) and hose spectra are trained against the XPS values, thereby obtaining a trained recipe.

Then, the full Spectral Reflectometry map is analyzed, and all spectra are interpreted with the trained recipe. For the "small sample" subset of spectra, the identical values are obtained back (as-trained), and for the other spectra, a neural network interpolation/extrapolation of the trained values is obtained.

In the above examples, "small" or sparse sampling plan provides a 5-point (or 9-point) map measured by the XPS, and "large" or dense sampling plan provides "full wafer map" measured by Spectral Reflectometer. The "large map" is analyzed to select therefrom the dies that have also a "small map" equivalent (for example, if XPS measures center and 4 points at the edges, then from the large map that includes all dies only center and the 4 points at the edges are selected). The optical data is interpreted with modeless recipe, e.g. train on 5, interpret on 65. In other words, this is a "natural extrapolation" (based on spectral data). The recipe per wafer is built. It should be noted that this method can be combined with standard modeless techniques, and provide an intermediate way where train for one wafer is used, and then verification and re-train only may be needed, or the other wafer is added to the training set as well, and so on.

It should also be noted that that the technique utilizes "on-the-fly training". Indeed, small sampling plan is applied with the first measurement tool, then large sampling plan data is collected with the second measurement tool, and interpretation of data for the second measurement tool includes the following: the samples set that match between the first and second tools' measurements are identified, training is performed with respect to that sample set to create temporary trained recipe, this is used to interpret measured data from the large sample set of the second measurement tool, and the temporary trained recipe is not needed anymore. It should be understood that this technique is fundamentally different from the standard training, where DOE is designed, trained, and saves as "the" recipe for all other wafers. On the contrary, in the invention, this is a recipe per wafer obtained by "on-the-fly training".

What is claimed is:
1. A measurement method for in-line measurements of one or more parameters of thin films in structures progressing on a production line, the method comprising:
applying X-Ray Photoelectron Spectroscopy (XPS) measurements to a first selected set of a small number of measurement sites in a thin film and providing XPS measured data, the thin film disposed on a structure;

applying optical measurements to a second set of a higher number of the measurements sites including the measurement sites of the first set and providing optical measured data;

processing the XPS measured data and determining a value for at least one parameter of the thin film in each of the measurement sites of said first set; and utilizing said at least one parameter value for interpreting the optical measured data, thereby obtaining data indicative of distribution of values of said at least one parameter within thin film, said distribution being indicative of quality of a process applied to said structure in production.

2. A system for use in the in-line measurements of one or more parameters of thin films in structures progressing on a production line, the system comprising:

a first measurement device configured to:
perform first type measurements according to a first, sparse sampling plan, and
provide first measured indicative of at least one parameter of a thin film in a first selected set of a small number of measurement sites in the thin film, the thin film disposed on a structure;

a second optical measurement device configured to:
perform second type measurements according to a second, dense sampling plan, and
provide second measured data indicative of at least one parameter of the thin film in a second set of a higher number of the measurements sites; and a control system configured to:
process the first measured data and determine at least one value of at least one parameter of the thin film in each of the measurement sites of said first set, and
utilize said at least one parameter value for interpreting the second measured data, and obtain data indicative of distribution of values of said at least one parameter within said second set of measurement sites.

3. The system of claim 2, comprising:
a controller configured to control the first and second measurement devices to perform said measurements according to, respectively, said sparse sampling plan and said dense sampling plan for selected measurement sites, wherein the measurement sites of said second set are selected to be substantially uniformly distributed within the thin film being measured.

4. The system of claim 3, wherein said controller is configured to select said second set of the measurement sites including said first set of the measurement sites.

5. The system of claim 3, wherein said controller is configured to select said first set of the measurement sites to enable measurement of minimal and maximal values of said at least one parameter in said selected measurements sites.

6. The system of claim 5, wherein said controller is configured to utilize data indicative of a shape of variation of said at least one parameter of the thin film across the structure for said selection of the first set of the measurement sites.

7. The system of claim 2, wherein to utilize said at least one parameter value for interpreting the second measured data, the control system is configured to:
identify a matching set between the measurement sites in the first and second measured data; and
create a temporary trained recipe for said matching set, and use said temporary trained recipe to interpret the second measured data.

8. The system of claim 2, wherein the first measurement device and the second measurement device are different from one another in at least time required for collection and interpretation of measured data, the first type measurements being relatively slow measurements and the second type measurements being relatively fast measurements.

9. The system of claim 8, wherein the first type measurements performed by the first measurement device are characterized by higher accuracy as compared to the second type measurements.

10. The system of claim 2, wherein the first type measurement device is configured to perform X-Ray Photoelectron Spectroscopy (XPS) measurements.

11. The system of claim 2, wherein the second type measurement device comprises Spectral Reflectometer.

12. The system of claim 2, wherein the at least one parameter of the thin film comprises thickness of the thin film.

13. The system of claim 2, wherein the structure comprises a semiconductor wafer.

* * * * *